(12) United States Patent
Cioanta et al.

(10) Patent No.: US 9,095,632 B2
(45) Date of Patent: Aug. 4, 2015

(54) METHODS FOR CLEANING AND TENDERIZING ANIMAL MEAT WITH SHOCK WAVES

(71) Applicant: SANUWAVE, INC., Alpharetta, GA (US)

(72) Inventors: Iulian Cioanta, Milton, GA (US); Yannick Spenninck, Lawerencville, GA (US)

(73) Assignee: Sanuwave, Inc., Alpharetta, GA (US)

( * ) Notice: Subject to any disclaimer, the term of this patent is extended or adjusted under 35 U.S.C. 154(b) by 0 days.

(21) Appl. No.: 14/228,976

(22) Filed: Mar. 28, 2014

(65) Prior Publication Data

US 2014/0212554 A1  Jul. 31, 2014

Related U.S. Application Data

(62) Division of application No. 13/719,964, filed on Dec. 9, 2012, now Pat. No. 8,685,317, which is a division of application No. 12/884,511, filed on Sep. 17, 2010, now Pat. No. 8,343,420.

(60) Provisional application No. 61/243,426, filed on Sep. 17, 2009.

(51) Int. Cl.
| | | |
|---|---|---|
| *A61L 2/00* | (2006.01) | |
| *B06B 1/00* | (2006.01) | |
| *A61L 2/025* | (2006.01) | |
| *A23L 3/015* | (2006.01) | |
| *B06B 3/04* | (2006.01) | |
| *A61L 2/02* | (2006.01) | |
| *A23B 4/015* | (2006.01) | |
| *A23L 1/318* | (2006.01) | |

(52) U.S. Cl.
CPC ............... *A61L 2/025* (2013.01); *A23B 4/015* (2013.01); *A23L 1/3187* (2013.01); *A23L 3/015* (2013.01); *A61L 2/02* (2013.01); *B06B 3/04* (2013.01); *A61L 2202/11* (2013.01); *A61L 2202/14* (2013.01); *A61L 2202/22* (2013.01); *A61L 2202/23* (2013.01); *A61L 2202/24* (2013.01)

(58) Field of Classification Search
CPC ............... A61L 2/00; C02F 1/00; C12H 1/00
USPC ............... 422/1, 20, 127–128; 435/173.1; 210/748.02; 250/432 R, 455.11, 492.1; 601/2; 604/5.02, 6.08, 9.09, 19
See application file for complete search history.

(56) References Cited

U.S. PATENT DOCUMENTS 6,168,814 B1 * 1/2001 Long ............................ 426/238

* cited by examiner

*Primary Examiner* — Monzer R Chorbaji
(74) *Attorney, Agent, or Firm* — Hunton & Williams, LLP

(57) ABSTRACT

This invention includes methods for cleaning and tenderizing animal meat with shock waves by submerging animal meat in a volume of fluid in a treatment tank including a shock wave applicator with a focal volume in the volume of fluid, and applying a pressure shock wave pulses to the animal meat from the shock wave applicator in sufficient amounts to eliminate biological contaminants and/or tenderize the animal meat.

20 Claims, 15 Drawing Sheets

US 9,095,632 B2

METHODS FOR CLEANING AND TENDERIZING ANIMAL MEAT WITH SHOCK WAVES

CROSS-REFERENCE TO RELATED APPLICATIONS

The present application is a divisional of U.S. patent application Ser. No. 13/719,964 filed Dec. 9, 2012, which is a divisional of Ser. No. 12/884,511 filed Sep. 17, 2010, now U.S. Pat. No. 8,343,420, which claims the benefit of priority of U.S. Provisional Application No. 61/243,426 filed Sep. 17, 2009, which are incorporated herein by reference.

BACKGROUND

When extracorporeal lithotripsy was developed and used for the treatment of kidney stones, it was observed that the pressure shock waves may have an anti-bacterial effect. Some of the kidney stones incorporate bacteria in them (due to their bacterial etiology) and after stone fragmentation, a higher rate of infection was expected, at least until the stone fragments were passed naturally. That was not the case when lithotripsy pressure shock waves were used, which pointed out toward bactericidal effect of the pressure shock waves. The same bactericidal phenomenon was observed during wound treatment using pressure shock waves.

The above-mentioned observations triggered extensive pre-clinical studies using laboratory cell cultures or animals. These studies showed that pressure shock waves can destroy, reduce proliferation of most common Gram positive and Gram negative, aerobic and anaerobic bacteria or break bacterial biofilms. The targeted bacteria included *Staphylococcus aureus*, Methycillin-resistant *Staphylococcus aureus* (MRSA), *Streptococcus mutans, Actinomyces naeslundii, Porphyromonas gingivalis* and *Fusobacterium nucleateum*.

The killing of bacteria is suggested to result from a combination of the following mechanisms:
  strong mechanical forces generated by pressure shock waves that can disrupt biofilms;
  cavitation microjets generated by collapsing cavitation bubbles can kill bacteria or disrupt biofilms;
  localized thermal effects produced by collapsing cavitation bubbles can also kill bacteria; and
  shock waves generated free radicals can have a destructive effect on bacteria or biofilms.

A similar effect as the one observed for bacteria was also shown in viruses. Based on preclinical studies, it is suggested that pressure shock waves can disrupt the outer membrane of the viruses and the bacteria that hosts the virus and thus killing them.

Another important observation from prior studies is that the membrane of the viruses and bacteria seems to be less flexible when compared with normal tissue cells or fluidic cells (as red blood cells), which makes bacteria and viruses more prone for destruction by the combined mechanisms generated by the pressure shock waves (compressive pressures combined with high velocity cavitation microjets).

Based on the above observations, a need exists to adapt the use of pressure shock waves in order to eliminate bacteria from fluids or from solid networks that might be filled with fluids. Further, a need exists to similarly use shock waves to disrupt viruses (immunodeficiency virus—HIV, hepatitis viruses, papilloma virus, herpes simplex virus, etc.) and to kill different micro-organisms such as giardia lamblia, legionella, cryptosporidium, and the like.

DESCRIPTION OF THE INVENTION

Blood Cleaning/Sterilization

Blood is an important human body fluid and is required for transfusions during medical interventions or for treating different diseases related to blood. The fact that blood goes everywhere in the body to bring nutrients to the living tissue makes it a very important part of the human/animal body. The blood can sustain life or bring bacteria and viruses and thus infection to organs/tissue/cells. This is why a healthy blood is vital for a healthy human/animal or to treat different diseases, infections that might affect human or animal bodies.

For medical purposes, blood is usually collected from healthy individuals, stored in plastic containers and administered as needed during medical procedures. Healthy volunteers/donors have to pass extensive background check and then the collected blood is tested for different pathogens that might be transmitted through blood. The collected blood, as of today, cannot be sterilized with existing cleaning/sterilization methods, due to their negative impact on blood. Thus radiation is not recommended, chemical cleaning/sterilization the same, and heat methods can coagulate the blood, which is not desired, etc. Accordingly, a method that can be used to sterilize the blood is an important need to allow the building of a larger blood supply for hospitals or to use for auto-transfusions (use the patient's own blood after cleaning/sterilization) for individuals that need blood to treat their afflictions.

The utilization of pressure shock waves to destroy pathogens, such as bacteria, viruses and other micro-organisms, is described in different method and design embodiments for eliminating contaminants from blood. In some embodiments, a method of the invention can be applied without physical contact with the blood and without destructive effects on desired blood components (leukocytes, lymphocytes, red blood cells, and platelets).

In methods of the invention, pressure shock waves can be produced using electrohydraulic, piezoelectric, electromagnetic, or blast pressure principles. Also, the pressure shock waves can be focused, unfocused, planar, pseudo-planar or radial. The pressure shock waves should have a high compressive phase followed by a strong tensile phase that produces significant cavitation. The high velocity cavitation microjets generated during collapse of the cavitation bubbles play an important role in permanently breaching the membrane of the bacteria and viruses and thus destroying them.

In various embodiments, the blood moves through sterile containers/pipes/tubes in close association with a shock wave source. In other embodiments containers or bags filled with blood can be exposed to pressure shock waves by moving the pressure shock waves applicator around the container/bag.

Embodiments to produce blood cleaning/sterilization are further described. It will be appreciated that in other embodiments different fluids may be similarly treated.

Figure 1:
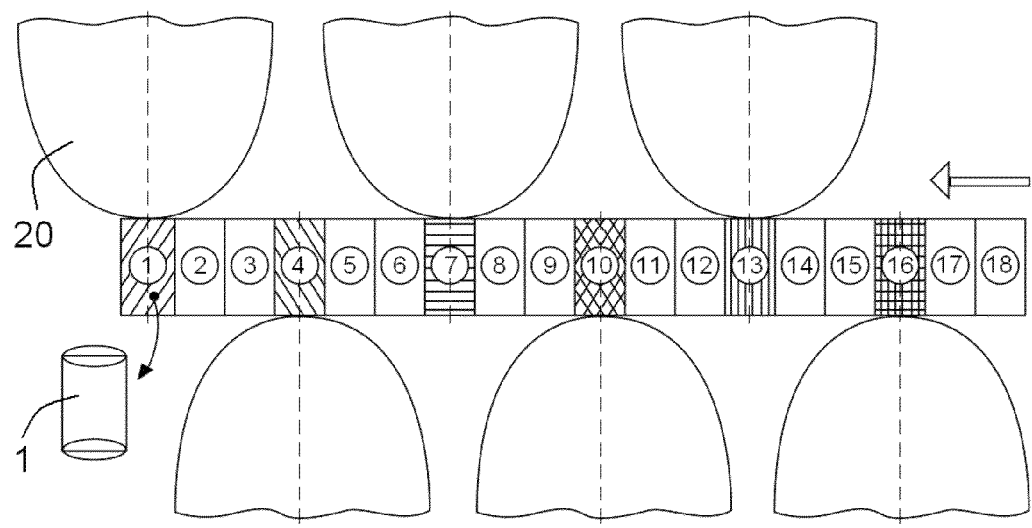
FIG. 1 is a schematic diagram of containers of blood in a shockwave treatment system in one embodiment of the present invention.

Referring to FIG. 1, blood containers 1 to 18 sit on a conveyer-type advancing system that moves in front of the pressure shock wave applicators 20, as indicated by the arrow. In the embodiment of FIG. 1 six (6) applicators 20 are used. The total number of applicators 20 may be selected by the desired productivity of the system. In an exemplary embodiment at least four (4) applicators 20 are provided.

As shown in FIG. 1, containers 1, 4, 7, 10, 13 and 16 are treated simultaneously by six applicators 20 in one position of the conveyer belt. After the cleaning/sterilization process is finished for containers 1, 4, 7, 10, 13 and 16, the conveyer belt moves with a distance equal with the diametric dimension of a containers (containers 1 to 18 have the same diametric dimension) and in this new position the system sterilizes the blood from containers 2, 5, 8, 11, 14 and 17. After enough pressure shock waves were delivered to containers 2, 5, 8, 11, 14 and 17, the conveyer moves again to align containers 3, 6, 9, 12, 15 and 18 with the corresponding applicators 20. Finally, after the complete cycle of cleaning/sterilization is applied to containers 3, 6, 9, 12, 15 and 18, the conveyer belt moves with a distance equal with a fresh batch series of eighteen (18) containers that will be treated in a similar manner as described above by the battery of applicators 20. Utilizing the above described sequence, the cleaning/sterilization of the blood is produced in an efficient manner. In embodiments, delivered shock waves are generated from 250 to 2,000 pulses/cm$^3$ of blood, with 5 kV-30 kV high voltage per discharge, with frequencies higher than 1 Hz and generating energies in the targeted area higher than 0.05 mJ/mm$^2$ and less than 0.9 mJ/mm$^2$).

The total number of applicators 20 used in a battery and the number of the containers 1 that can be used on the conveyer belt depends on the capacity of the cleaning/sterilization line and desired efficiency to assure an economical way to clean/sterilize the blood. Also, the arrangement presented in FIG. 1 can include computerized control of conveyer belt movement and timing of cleaning/sterilization for each container (1 to 18), including based on the type of contaminant or contaminants that is/are targeted during cleaning/sterilization process. Computer control provides flexibility for the whole cleaning/sterilization line. It will be appreciated that timing for the cleaning/sterilization chosen for a certain process is the largest time necessary to kill a certain contaminant (bacteria or virus) when the cleaning/sterilization process is targeting multiple contaminants. The selection of timing can be done automatically based on a selection menu included in the user interface of a software program that is running the cleaning/sterilization process.

Figure 2:
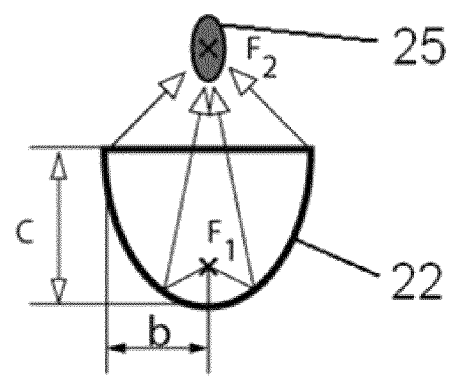
FIG. 2 is a schematic diagram of an ellipsoidal reflector and shock wave focal volume in one embodiment of the present invention.

The blood containers' (1 to 18) dimensions may be provided in such way to be completely encompassed within the dimensions of the focal volume of the pressure shock wave applicators 20, thereby allowing a complete flooding with high energy pressure shock waves of the entire container (1 to 18). The focal volume 25 is defined as the volume (cigar shape) in which the highest pressure gradients and energy concentrations are produced due to the shock waves focusing process (as can be seen in FIG. 2), when using a focusing reflector 22 that can be ellipsoidal, parabolic, spherical, etc., in shape (the reflector 22 is the main part of the applicators 20 construction). In FIG. 2 is presented an ellipsoidal reflector 22 that has its main characteristics defined by its major and minor elliptical semiaxes values. The ratio of the major semi-axis and minor semiaxis (c/b) dictates the dimensions of the focal volume 25. If the value of the ratio is closer to 1 the reflector 22 will generate almost a spherical focal volume 25 and the larger the ratio is (2 or higher) the reflector 22 will generate a broader and longer focal volume 25 (generally a cigar shape focal volume 25). Also, the focal volume 25 can become broader and longer with the decrease of reflector 22 diametric opening at its mouth (called also aperture). In general, the amount of energy deposited in the focal volume 25 is dependent on the surface area used by reflector 22 for focusing the pressure shock waves (the deeper reflectors 22 can generate more energy when compare with shallower reflectors 22).

The energy input settings (process values) can also influence the focal volume 25 dimensions used for the embodiment presented in FIG. 1. The higher the settings for the shock waves the larger the focal volume 25 can be. Therefore, based on the geometrical dimensions and materials used in construction of the pressure shock waves reflectors 22, on the type of shock wave source used (electrohydraulic, electromagnetic, piezoelectric, or blast) or on the energy input settings, the dimensions of the containers (1 to 18, as presented in FIG. 1) can be determined based on the desired applicators' 20 and reflectors' 22 dimensions and targeted utilization. Different geometries and different methods to produce pressure shock waves will provide different focal volumes 25. In general, the larger the dimension of the focal volume 25, the more efficiency is achieved.

For example, if the focal volume 25 is approximated to ø10×20 mm$^3$ (cylinder with 10 mm diameter and 20 mm in length/height), the blood containers (1 to 18) should have the same volume or smaller. These containers (1 to 18) are positioned on the respective designated slots of the conveyer. Then the conveyer brings them in front of the applicators 20 that will use pressure shock waves to kill contaminants from the blood.

Similar effects can be obtained if the blood is circulated at a very slow speed in front of the pressure shock wave applicators 20. In alternative embodiments to containers 1, a continuous pipe full of blood can be used for circulating the blood in front of the shock wave applicators 20. In this embodiment, the diameter of the pipe should match the smaller dimension of the focal volume 25 for the applicators 20 (for example if the focal volume 25 has a length of 20 mm and a diameter of 10 mm, then the dimension of the pipe for blood circulation should be diameter of 10 mm).

Figure 3A:
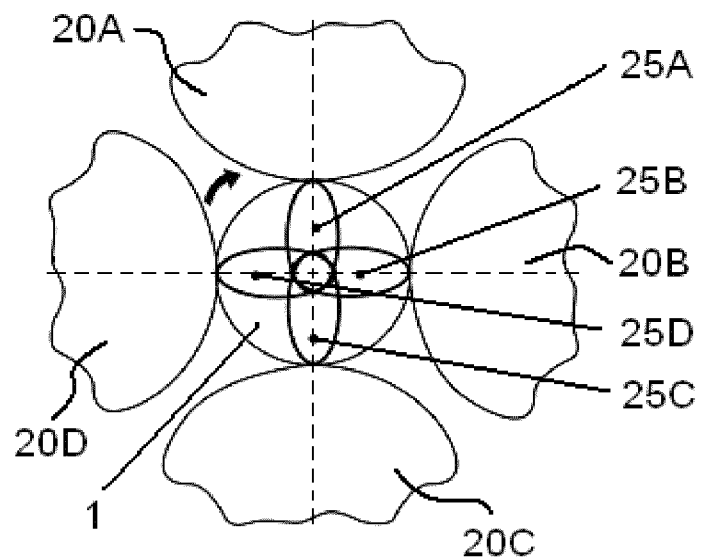
FIG. 3A is a top cross-sectional schematic diagram depicting multiple focal volumes from multiple shock wave applicators to a container in one embodiment of the present invention.
Figure 3B:
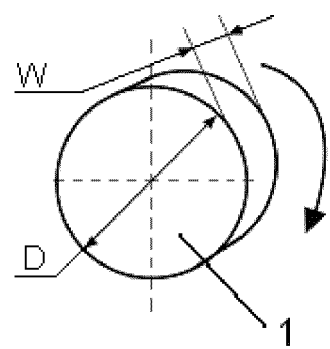
FIG. 3B is a top perspective view from above of a container in one embodiment of the present invention.

Referring to FIG. 3A, in an embodiment a blood container 1 made of a plastic that has acoustic impedance close to the water or blood is provided. In this embodiment, the container 1 is a cylinder of a larger dimension, due to the fact that the treatment container 1 is placed in an area where multiple focal volumes (25A, 25B, 25C and 25D produced by the corresponding applicators 20A, 20B, 20C and 20D) are intersecting. For example with a focal volume 25 of 20 mm in length and 10 mm in diameter, the container 1 could have a diameter "D" of 40 mm and a width "W" of 8-10 mm (see FIG. 3B). To sterilize the blood, the applicators 20A, 20B, 20C and 20D from FIG. 3A can be fired simultaneously or sequentially and the container 1 has a rotational movement in front of the applicators 20A, 20B, 20C and 20D (as seen in FIGS. 3A and 3B).

Figure 4:
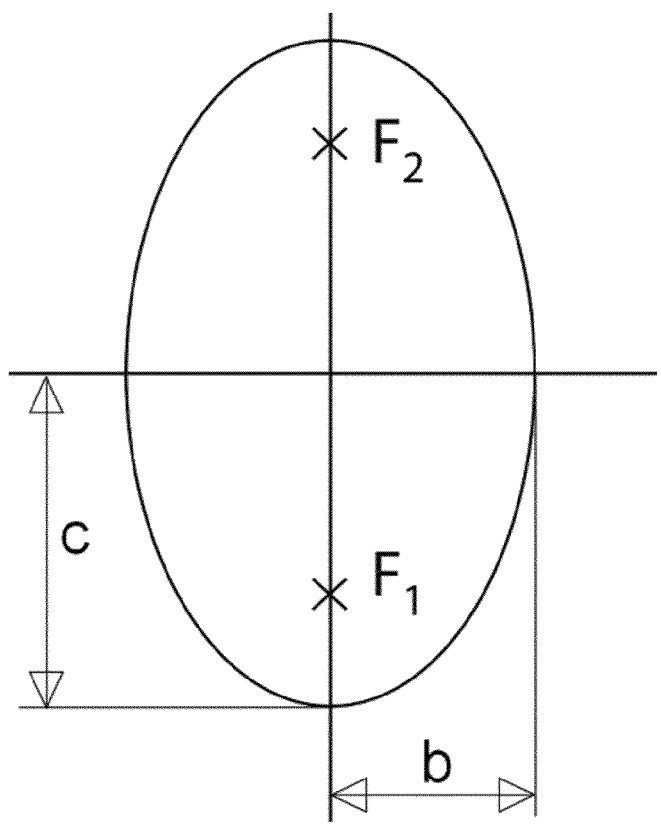
FIG. 4 is a schematic diagram of ellipsoidal shock wave reflector geometry and its focal points in one embodiment of the present invention.

To increase the focal volume 25 in the cleaning/sterilization area, and thus the volume of the blood containers 1, the ratio of the major and minor semi axes of the ellipsoid (c/b) can be increased, which will give an increase of the ellipsoid geometry and generally an increase in the reflector 22 area for the device, as shown in FIG. 4. A deeper reflector 22 (larger major semi axis c) will generally provide a longer and wider focal volume 25 and an increase in the minor semi axis "b" will give a decrease in the diameter and length of the focal volume 25. FIG. 4 also shows that the ellipsoidal geometry is characterized by the first focal point $F_1$ as the origination of the pressure shock waves and by the second focal point $F_2$ as the point where the focusing is targeted. $F_1$ in embodiments resides inside the reflector 22 of the applicator 20 and $F_2$ can in various embodiments be positioned before, in or after the targeted area for pressure shock waves treatment. In order to position the second focal point $F_2$ before, in or after targeted area for pressure shock waves treatment, only a portion of the ellipsoidal geometry is necessary in embodiments for focusing, such as half of the ellipsoidal geometry.

Figure 5:
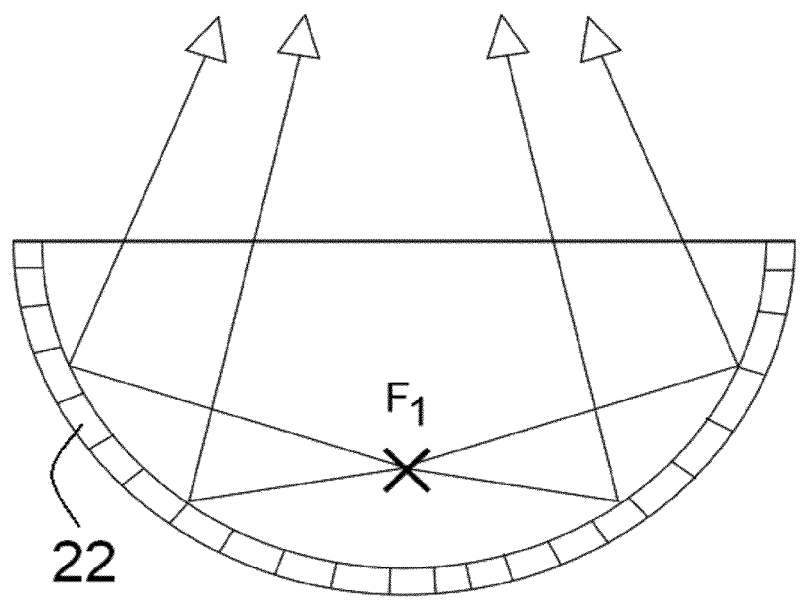
FIG. 5 is a cross-sectional schematic diagram of ellipsoidal shock wave reflector geometry that generates unfocused shock waves in one embodiment of the present invention.

Another method to increase the volume used for cleaning/sterilization is the use of unfocused devices (they do not have a defined focal volume 25 unlike focused devices), as presented in FIG. 5. In this embodiment the cleaning/sterilization is produced through high pressure gradients produced by the partial focusing and distortion of the spherical waves generated in $F_1$ (first focal point for the ellipsoidal geometry presented in FIGS. 4 and 5). These pressure gradients are found in the area where the blood containers 1 are placed for cleaning/sterilization.

Another option is given by pressure waves generated by radial devices. With the radial devices a field of high pressure is created that dissipates rapidly from the source inside the blood container 1. In this embodiment, there is generally no focal volume 25 present and alternatively a field of high pressure gradients is created in the treatment/cleaning/sterilization area, as described before for the unfocused devices, which creates pressure waves and not shock waves (shock waves are characterized by strong temporal and peak pressure distortions between the compressive and tensile portion of the wave). The high pressure gradient fields generated by unfocused or radial pressure waves can be also used for the embodiments presented in FIG. 1 and FIGS. 3A and 3B, which can significantly increase the size of the containers 1, an in embodiments the efficiency of the treatment.

In different embodiments, there is a tuning of the pressure values needed to kill different types of bacteria, viruses, and microorganisms, which will dictate the approach for a specific treatment (focused, explosive, unfocused or radial pressure waves). Multiple stations of pressure shock waves devices can be set for treating the same batch of blood containers 1 so that each station or individual device is tuned up for different pressure values that have specific action on a specific targeted type(s) of pathogen(s), to accomplish a desirable cleaning/sterilization of the blood.

The cleaning/sterilization of the blood can be applied to the whole blood (e.g. prior to any filtration) or to blood components after a filtration process or processes. The number of pulses delivered, energy setting and frequency of shock delivery (number of pulses per second) can be adjusted for the specific situation. For example, a treatment/cleaning/sterilization regiment may be applied differently and specifically for: whole blood, red blood cells, platelets; and serum.

It will be appreciated that specific parameters and methods applicable to specific components of blood (or other fluids) may be utilized in the various embodiments that are presented in this disclosure. Further, in some embodiments, specific targeted microorganisms, bacteria and viruses in the blood may be treated with shock waves under specific parameters individually more effective to the particular target.

In some embodiments, to eliminate residues of bacteria, viruses, DNA fragments and cells that did not survived the cleaning/sterilization progression, a filtration process after cleaning/sterilization may be used.

In other embodiments, the cleaning and sterilization process can be designed to use small and portable treatment units that can be utilized for field transfusions, such as in geographical areas of difficult access of for emergency medical purposes (e.g. military, disaster areas). These devices can be alternatively driven by connection to available energy sources or by batteries (rechargeable or non-rechargeable).

Figure 6A:
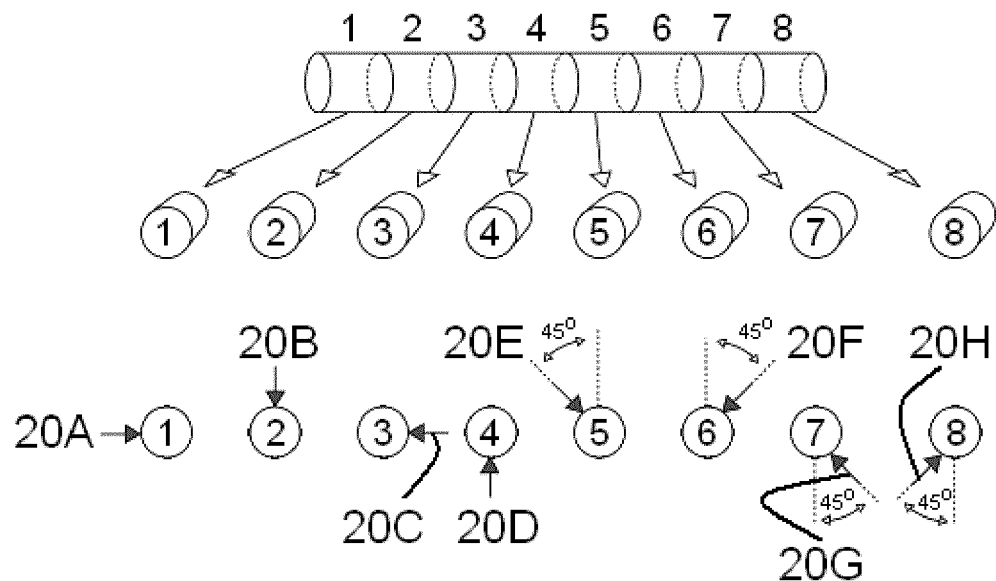
FIG. 6A is a schematic diagram depicting the angular positioning of multiple shock wave applicators along multiple segments of a pipe in one embodiment of the present invention.
Figure 6B:
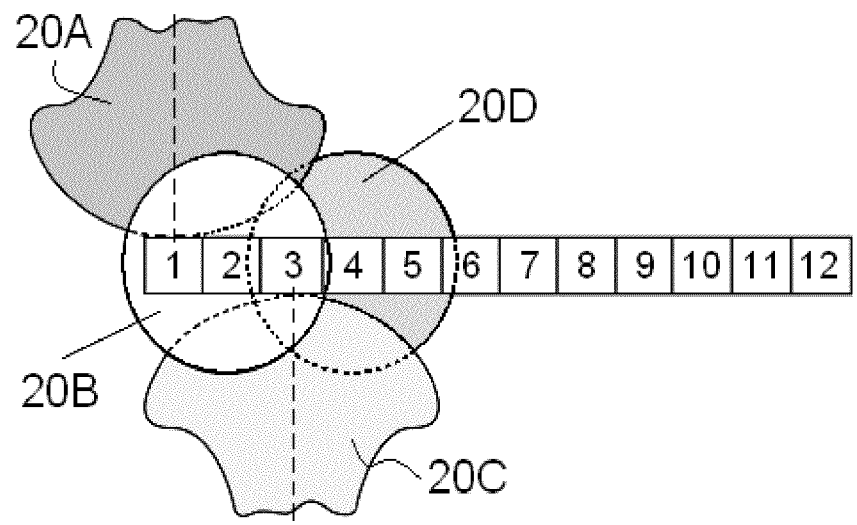
FIG. 6B is a schematic diagram depicting the actual positioning of multiple shock wave applicators along multiple segments of a pipe in one embodiment of the present invention.

Another arrangement for blood cleaning/sterilization, designed to increase efficiency is presented in the embodiment of FIGS. 6A and 6B.

FIG. 6A shows a sequence of blood containers 1 to 8 arranged end to end in a conveyor (such as similar to FIG. 1). In other embodiments the containers may alternatively be individual segments of a cylindrical pipe, and the individual views show an exemplary way to dispose shock wave applicators 20A, 20B, 20C, 20D, 20E, 20F, 20G and 20H in a 3D (spatial) manner (indicated by the direction of the arrows around the individual blood segments/containers 1 to 8) to produce optimum cleaning/sterilization of blood flowing through the cylindrical pipe or conveyed in containers 1 to 8. Such arrangement provides a highly efficient blood cleaning/sterilization process in embodiments of the invention. FIG. 6B depicts physical disposition around the pipe/conveyer of the applicators 20A, 20B, 20C and 20D (the applicators 20E, 20F, 20G and 20H are not shown). In embodiments the individual segments/containers 1 to 8 have dimensions comparable with the focal volumes 25 (not shown in FIG. 6B) produced by the applicators 20A, 20B, 20C, 20D, 20E, 20F, 20G and 20H. Also, the actual dimensions of the applicators 20A, 20B, 20C, 20D, 20E, 20F, 20G and 20H should allow them to be positioned with at least 90° angle intervals around the pipe and with an axial step equal with the length of each segments/containers 1 to 8.

The embodiment presented in FIGS. 6A and 6B (with containers) includes a forward movement/indentation for eight (8) sequential containers 1 to 8 (equal with the diametric dimension of the focal volume 25 of the applicators 20A, 20B, 20C, 20D, 20E, 20F, 20G and 20H) in one step compared with the previous embodiment presented in FIG. 1, which includes a forward movement for only one diametric dimension of the focal volume 25 for the first three (3) steps and then a fourth movement equal with 18 times the diametric dimension of the focal volume 25 for the 1 to 18 blood containers sterilized in the first three steps. The 4 (four) steps presented for solution from FIG. 1 will produce for the embodiment described in FIGS. 6A and 6B the cleaning/sterilization of 32 blood containers. The embodiment of FIGS. 6A and 6B uses 8 pressure shock waves applicators/heads, which means that if the same number of applicators/heads (8) are used in the embodiment of FIG. 1 the total number of containers sterilized in four (4) sequential steps is 24 compared with 32 for the embodiment FIGS. 6A and 6B, i.e. a 25% increase in efficiency.

Both embodiments presented in FIGS. 1 and 6A and 6B can also use continuous flow of blood through a pipe in front of the pressure shock waves applicators 20A to 20H, with a correct timing to the presence of blood in the targeted area to avoid under or over exposure to the pressure shock waves.

Figure 7:
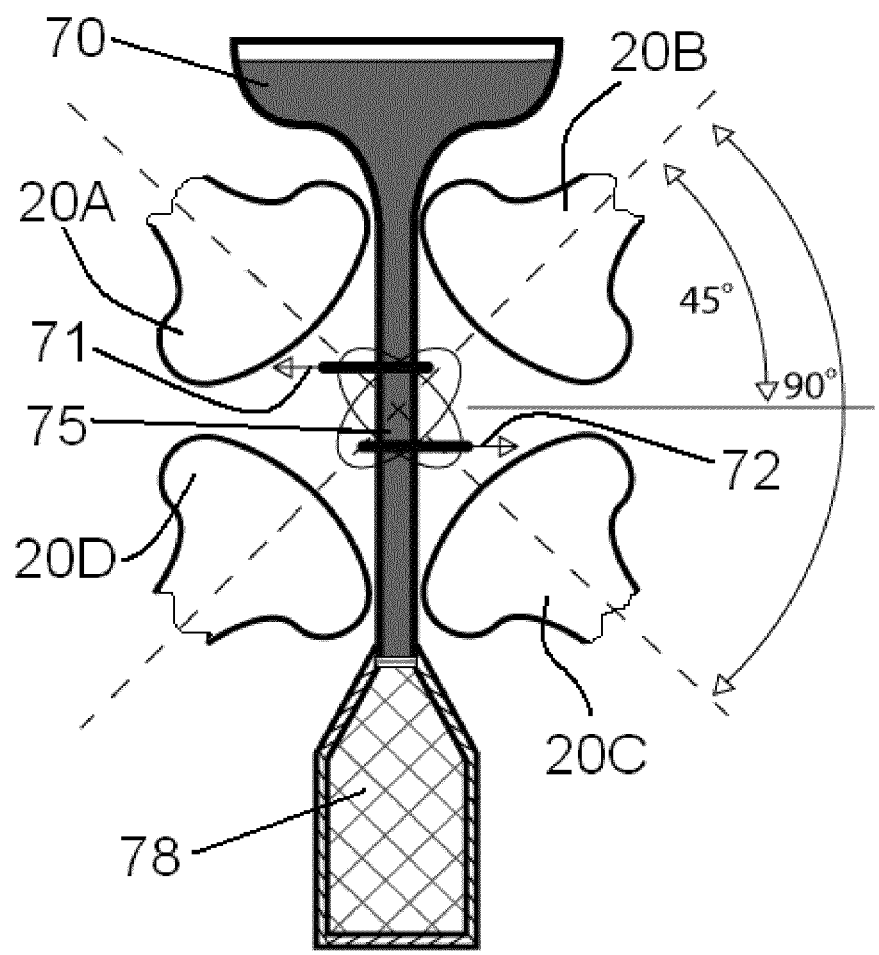
FIG. 7 is a cross-sectional schematic diagram of multiple shock wave applicators along a funnel device in one embodiment of the present invention.

For the embodiment presented in FIG. 7, the untreated blood is dropped in a funnel container 70 that goes in front of four (4) applicators 20A, 20B, 20C and 20D arranged symmetrically around the funnel container 70, to allow the overlap of their focal volumes. The overlap of focal volumes creates a targeted/treatment volume 75 in the funnel container 70 in between the two valves 71 and 72 (71 is identified as top valve of the funnel container 70 and 72 as the lower valve of the funnel container 70).

The targeted/treatment volume 75 enclosed in between valves 71 and 72 is a region where the combination of the focusing created by applicators 20A, 20B, 20C and 20D will generate an increased amount of energy that can be able to kill the most resistant bacteria, viruses or micro-organisms, due to overlap of individual focal volumes 25A, 25B, 25C and 25D (not specifically identified in FIG. 7).

In this embodiment the cleaning/sterilization process has the following steps:
1) with valves 71 and 72 closed the blood is placed in the upper funnel container 70
2) valve 72 stays closed and valve 71 is opened, which allows the blood to get in the designated targeted/treatment volume 75
3) valve 71 is closed and the cleaning/sterilization process is done to the designated targeted/treatment volume 75, by the applicators 20A, 20B, 20C and 20D
4) after the cleaning/sterilization is finished, valve 72 is opened, which allows the sterilized blood to go in the collection bag/container 78
5) valve 72 is then closed after the blood emptied the designated targeted/treatment volume 75
6) repeat steps 2 to 5 until the whole quantity of blood that can be received by the collection bag/container 78 is sterilized. After the collection bag/container 78 is filled in, it can be replaced by a new/empty collection bag/container 78. The replacement of the collection bags/containers 78 must be done all the time with the valve 72 in closed position.

Figure 8:
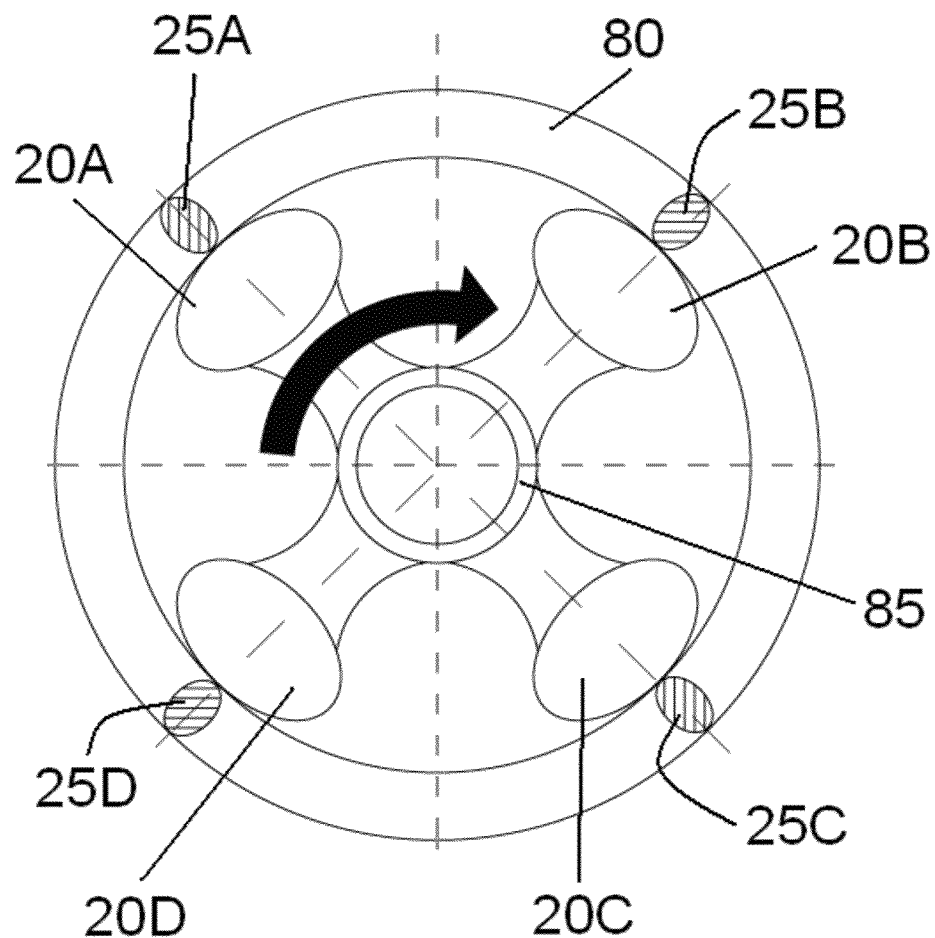
FIG. 8 is a top cross-sectional schematic diagram of circumferential fluid tube and rotatable shock wave applicators in one embodiment of the present invention.

In the embodiment presented in FIG. 8 the circumferential blood/fluid tube 80 is fixed and the applicators 20A, 20B, 20C and 20D are mounted on an applicators' rotator 85, which allows the rotational movement (indicated by the arrow) of the applicators 20A, 20B, 20C and 20D to produce the necessary treatment/cleaning/sterilization of the blood. In this way the focal volumes 25A, 25B, 25C and 25D (produced by the applicators 20A, 20B, 20C and 20D) are moved along the circumferential blood/fluid tube 80 with a predetermined speed to allow complete exposure of the blood to the pressure shock waves and thus the complete cleaning/sterilization of the blood enclosed in the circumferential blood/fluid tube 80 is done. After cleaning/sterilization cycle the circumferential blood/fluid tube 80 is removed from the fixture and a new one is attached for a new cleaning/sterilization cycle. This method, as in the previous embodiments, can be fully automated using robotic and computerized systems to increase productivity and provide adaptability to the specific pathogen or pathogens targeted by the blood cleaning/sterilization cycle.

Figure 9:
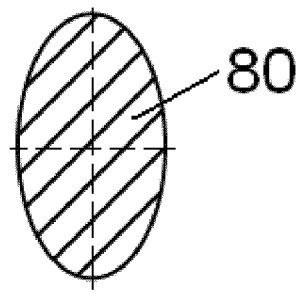
FIG. 9 is a cross-sectional plan view of a circumferential fluid tube in one embodiment of the present invention.

Referring to FIG. 9, the cross section of the circumferential blood/fluid tube 80 is shown to mimic the focal volumes 25A, 25B, 25C or 25D in size and shape.

Figure 10:
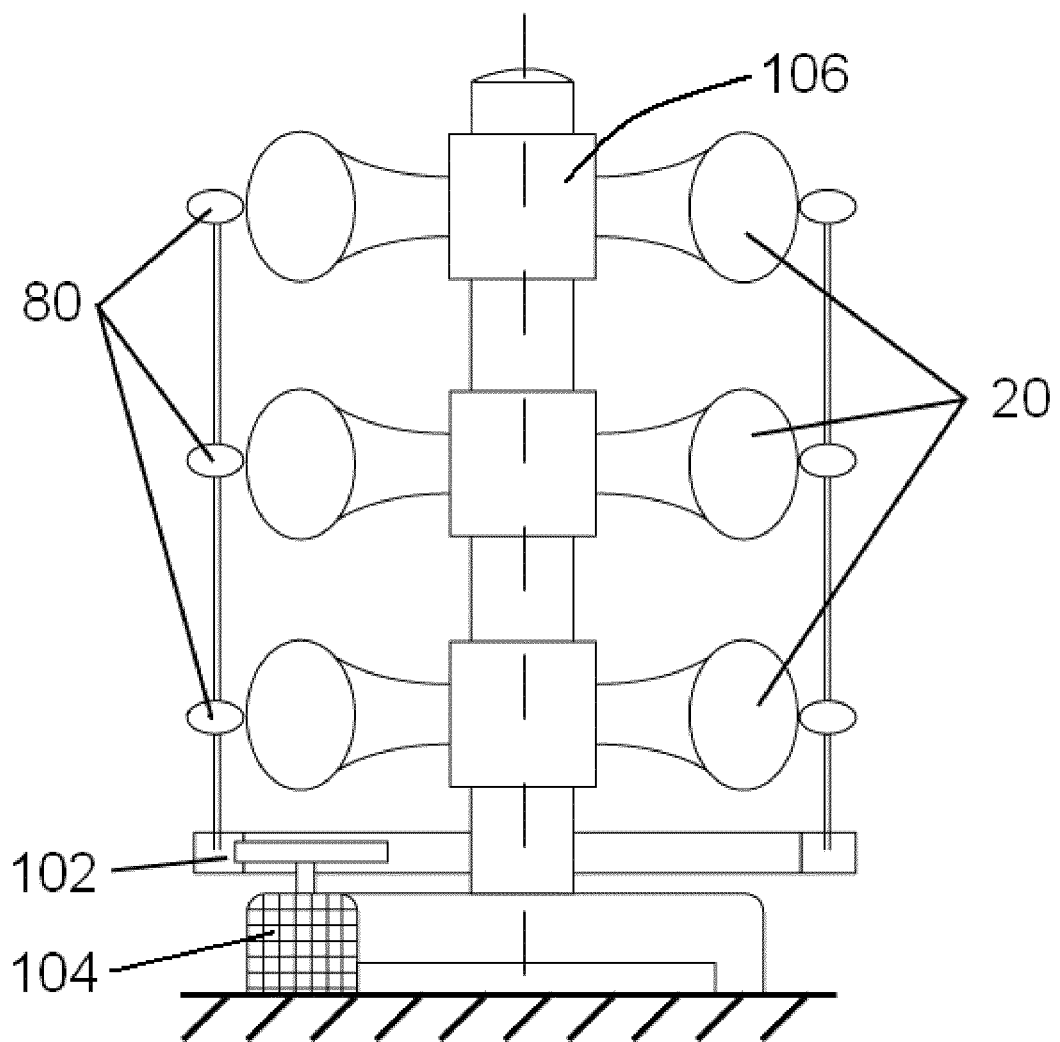
FIG. 10 is a cross-sectional schematic diagram of multiple rotatable circumferential tubes and stationary central shock wave applicators in one embodiment of the present invention.

In the embodiment shown in FIG. 10, multiple applicators 20 are attached on fixed mounting structure 106 and the circumferential blood/fluid tubes 80 have a motorized circumferential movement around the applicators 20, via a gear mechanism 102, which is driven by the rotator motor 104. Also, FIG. 10 shows three applicators 20 and circumferential blood/fluid tubes 80 that form stations in a vertical stacking construction, for improved efficiency. In this embodiment, the movement of the circumferential blood/fluid tubes 80 in front of the applicators 20 is done with a predetermined speed to allow complete exposure of the blood to the pressure shock waves and thus desirable cleaning/sterilization of the blood enclosed in the circumferential blood/fluid tubes 80 is accomplished.

This arrangement can be also fully automated using robotic and computerized systems to increase productivity and provide adaptability to the specific pathogen or pathogens targeted by the blood cleaning/sterilization cycle.

Figure 11:
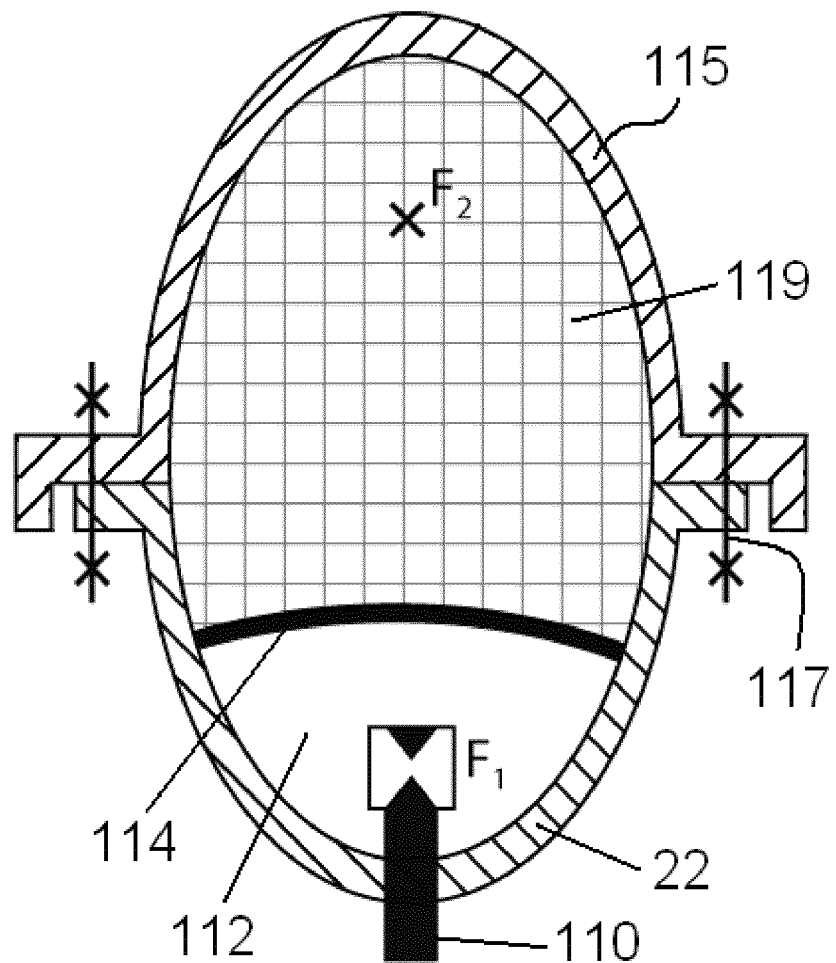
FIG. 11 is a cross-sectional schematic diagram of full ellipsoidal reflector with the upper shell of a shock wave device including a bag of fluid to be treated in one embodiment of the present invention.
Figure 12A:
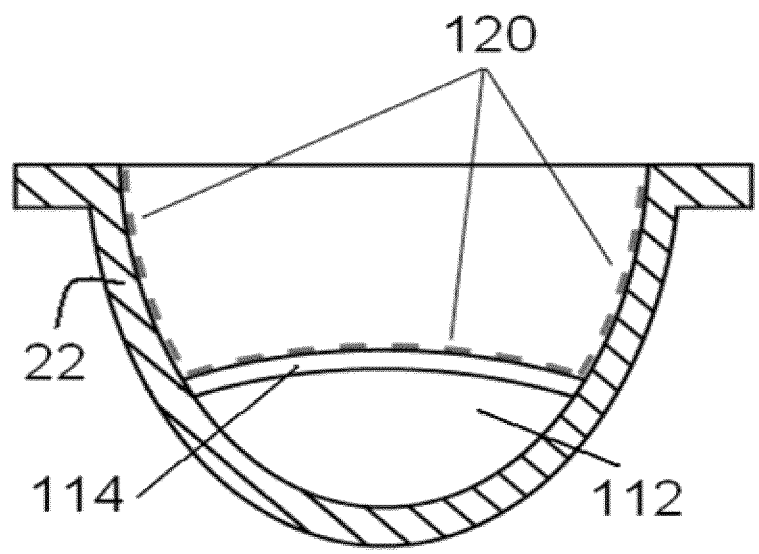
FIG. 12A is a cross-sectional schematic diagram of ellipsoidal reflector of an electrohydraulic shock wave device with a bag-contacting surface in one embodiment of the present invention.
Figure 12B:
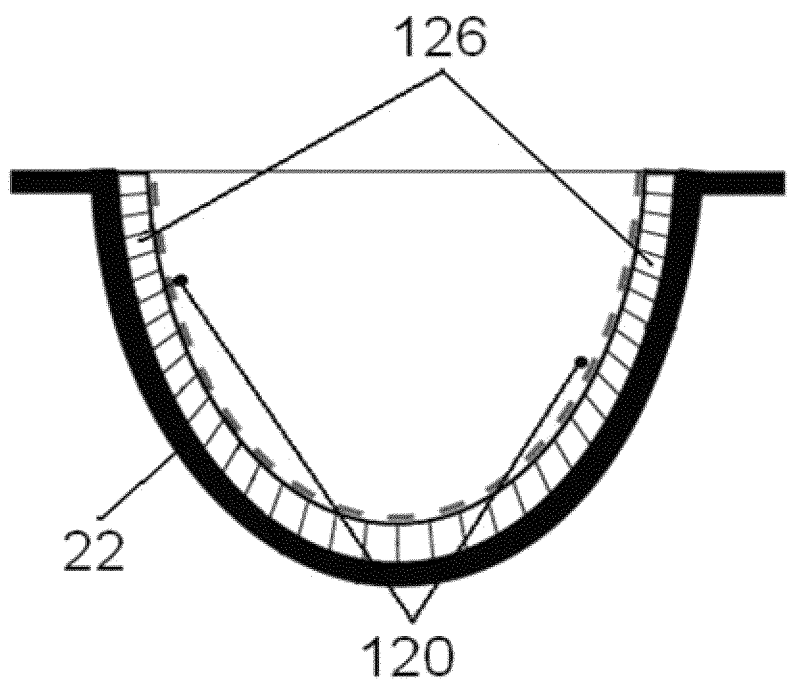
FIG. 12B is a cross-sectional schematic diagram of ellipsoidal reflector of a piezoelectric shock wave device with a bag-contacting surface in one embodiment of the present invention.

FIG. 11 shows another embodiment with a blood bag in a shock wave applicator device that can be used for blood cleaning/sterilization. With further reference to FIGS. 12A and 12B electrohydraulic and piezoelectric principles used to produce pressure shock waves are shown as well-suited to the bag-treatment embodiment of FIG. 11.

In the embodiment of FIG. 11 the upper shell 115 of an ellipsoid geometry is used to create a full ellipsoid together with the reflector 22, which allows the usage of the whole surface of the ellipsoid for focusing the pressure shock waves. In this way a field of pressure gradients is created in the whole volume of the ellipsoid, which in principle doubles the efficiency compared with classical construction of reflectors 22, which use only 50% of an ellipsoid surface to focus pressure shock waves (they represent half an ellipsoid). With such approach, the volume of blood sterilized in one session is thus increased and the cleaning/sterilization process is produced in a shorter period of time compared with methods and constructions described in other embodiments.

The upper shell 115 and the reflector 22 are kept together using the locking/latching devices 117. The focusing can still be generated with this embodiment, although on the way to the focus the pressure gradients generated during focusing process inside the ellipsoid are high enough to themselves kill bacteria/viruses. The milder pressure gradients generated in such embodiment, when compared with the pressure values from the focal volume 25, provide a milder option to kill bacteria, viruses or micro-organisms.

In order to produce the pressure shock waves for the electrohydraulic embodiment presented in FIG. 11, the pressure shock waves will originate from $F_1$ where a high voltage discharge in water/propagation medium 112 is produced in between two opposing electrodes 110. The water/propagation medium 112 volume is contained in between the bottom of the reflector 22 and the membrane 114. The membrane 114 is also used to isolate the water/propagation medium 112 from the cleaning/sterilization zone. The volume of the blood bag 119 can match the volume of the actual cleaning/sterilization zone, for maximum efficiency. Due to the presence of the membrane 114 in order to allow a good propagation of the shock waves from the water/propagation medium 112 through the membrane 114 and into the blood bag 119, a good coupling must be accomplished in between the membrane 114 and the blood bag 119 by using a coupling ultrasound gel. As shown in FIG. 11, the blood bag 119 sits on top of the membrane 114 where a coupling gel is applied in embodiments. The gel may also applied to the coupling between the blood bag 119 and the upper shell 115 of the ellipsoid.

The same coupling principle applies to all the coupling surfaces between different components presented in embodiments from this patent. Thus the components that are intersected by the propagating pressure shock waves must use a coupling substance in order to avoid diffraction and reflection of the shock waves, or the loss of energy at the boundaries between different substances/materials of very different acoustic impedance (for example water and air have very different acoustic impedances and this is why this mismatch must be avoided during pressure shock waves propagation).

An important feature of the same embodiment presented in FIG. 11 is given by the fact that the pressure gradient creates a movement (stirring effect) inside the bag, resulting in homogeneous treatment of the whole volume blood bag 119.

A piezoelectric embodiment (as presented in FIG. 12B) will not need the water/propagation medium 112 reservoir and the membrane 114, as presented in the electrohydraulic embodiment of FIGS. 11 and 12A. However, the blood bag/container coupling surface 120 of the reflector 22 is still present in both electrohydraulic reflector 22 (presented in FIG. 12A) or for the piezoelectric reflector 22 presented in FIG. 12B.

The piezoelectric embodiment of FIG. 12B provides more space for the blood bag 119, which now can fill completely the bottom portion of the reflector 22. This is possible because the piezoelectric elements 126 can be disposed on the surface of the reflector 22 and thus the pressure shock waves emanate directly from the reflector 22 surface, without the need of a dedicated space for a spark discharge in between two opposing electrodes 110, as presented in FIG. 11.

Figure 13:
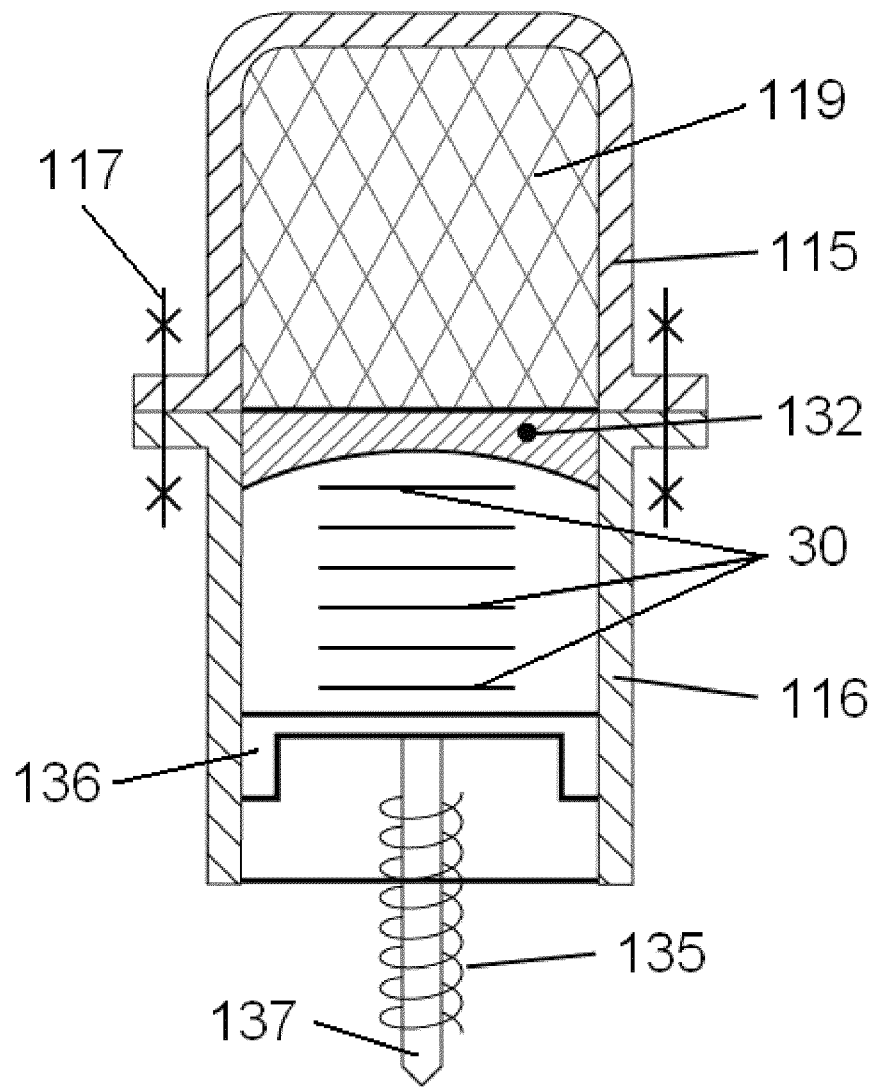
FIG. 13 is a cross-sectional schematic diagram of an electromagnetic shock wave device with unfocused waves delivered to a bag of fluid in one embodiment of the present invention.

In another embodiment shown in FIG. 13, pressure shock waves produced using the electromagnetic principle and an unfocused approach may be used to treat blood bag 119.

Cleaning/sterilization in this embodiment is induced by pressure gradients, without any focusing or focal volume 25 presence. The lens 132 forms a separation between the upper chamber, where the blood bag 119 is found inside the upper shell 115, and the lower chamber formed in between the lens 132, lower shell 116 and the electromagnetic wave transmitter/piston 136. The upper shell 115 and the lower shell 116 are kept together using the locking/latching devices 117. The electromagnetic planar waves 30 are generated inside the lower shell 116 by the electromagnetic coil/trigger 135 that makes the electromagnetic wave transmitter 136 to vibrate in the vertical direction due to the movement of the blasting piston 137 when a current is passed through the electromagnetic coil/trigger 135. The lens 132 collects the planar waves 30 generated in the lower chamber and then distribute them (still in a planar form) into the blood bag 119.

Cleaning of Harvested Human and Animal Tissue for Implantation

The cleaning/sterilization effect of pressure shock waves can be used for human or animal tissue that was harvested for human implantation. This harvested tissue needs to be cleaned of any contaminants (bacteria, viruses, micro-organisms, etc.) in order to avoid any immune reaction for the recipient.

Such tissues may include, for example, soft tissue (e.g. skin, tendons, ligaments, etc.); or hard tissue (e.g. bone, cartilage, etc.).

The pressure shock waves applied to the harvested tissue can help to clean the scaffolding (collagen matrix, bone matrix) out of unwanted germs brought into the tissue by the blood circulation.

Figure 14:
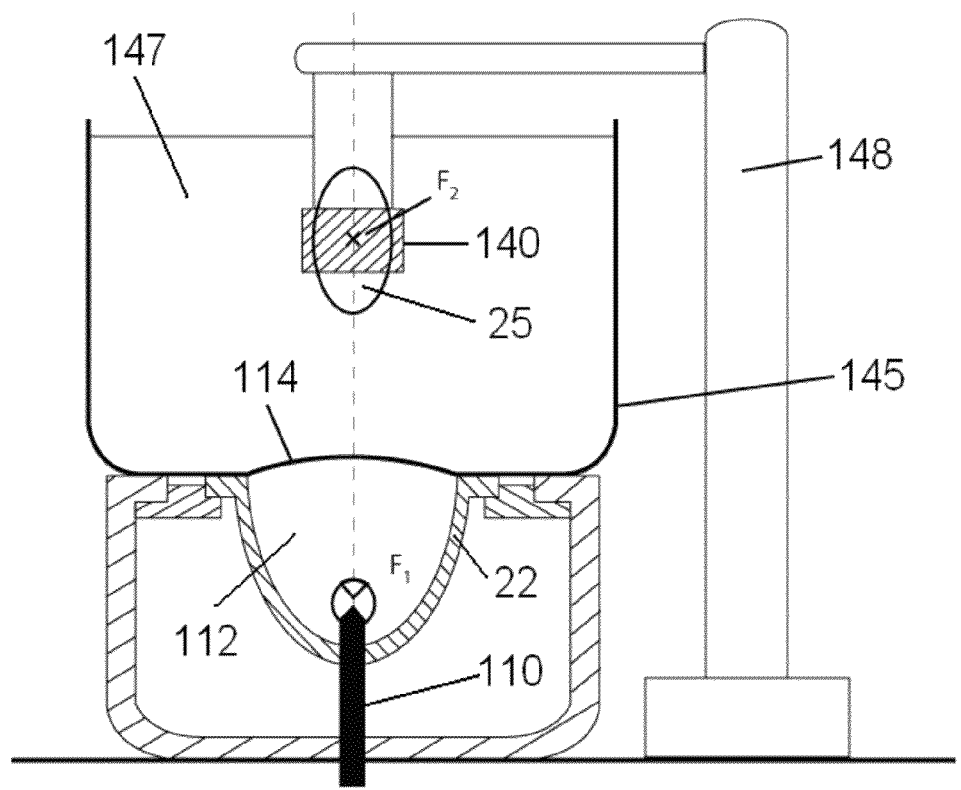
FIG. 14 is a cross-sectional schematic diagram of a shock wave application system that targets a tissue sample suspended in a bath in one embodiment of the present invention.

When the harvested tissue has a small size, it can be suspended in a saline bath (or any other fluid that it is used in the cleaning and processing of the tissue) and treated in a fixed position without the need to move the sample around in the field targeted by the pressure shock waves, as shown in FIG. 14.

This embodiment is practical only when the dimensions of the tissue 140 are comparable with the dimensions of the focal volume 25. The tissue can be suspended directly in the saline or using a special designed basket, which will not interfere with the shock wave propagation.

As shown in FIG. 14, on top of the reflector 22 a membrane 114 is used to create an enclosed chamber in which the high voltage discharge of the opposing electrodes 110 is produced inside the water/propagation medium 112 in order to generate electrohydraulic pressure shock waves. The membrane 114 is also used to create the coupling of the reflector 22 with the holding vessel 145 in which the cleaning is made. The material of the membrane 114 allows the good propagation of the pressure shock waves from the reflector 22 to the fluid/saline 147 that fills the holding vessel 145 and surrounds the tissue 140. The correct positioning of the tissue 140 relatively to the focal volume 25 of the reflector 22 is realized via the tissue support fixture 148.

Figure 15:
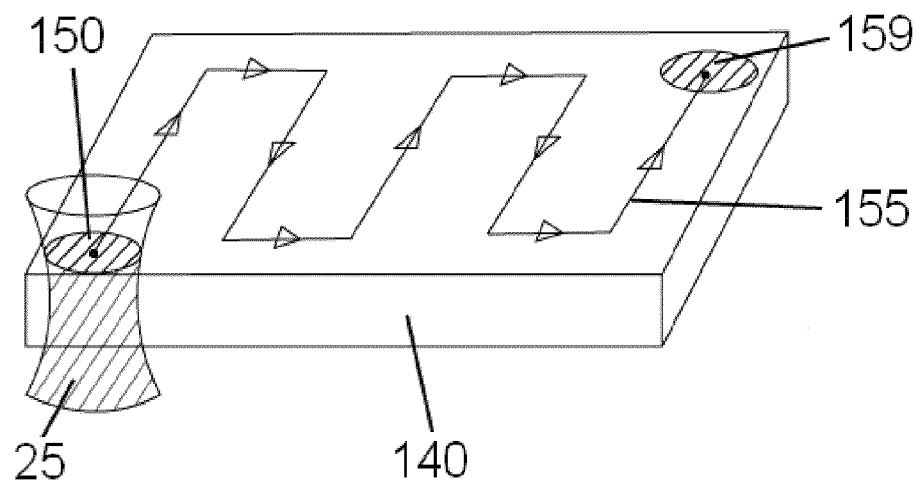
FIG. 15 is a schematic diagram of a movable shock wave applicator and movement path across a tissue in one embodiment of the present invention.

In general for cleaning/sterilization of the human or animal tissue that was harvested for human implantation is desired to obtain energies in the treatment area between 0.10 and 1.20 mJ/mm$^2$ and use frequencies of pulses per second between 1 Hz and 12 Hz. The energy necessary to treat the tissue sample is dependent on the type of tissue that is cleaned/sterilized. A high energy setting (energy flux density between 0.40 and 0.90 mJ/mm$^2$) combined with high number of pulses (higher than 1,000 pulses/cm$^3$) is used in various embodiments for hard tissue cleaning. Lower energy settings (energy flux density between 0.10 and 0.40 mJ/mm$^2$) and lower number of shocks/pulses (50 to 500 pulses/cm$^3$) is used in various embodiments for soft tissue cleaning. In certain embodiments, different settings (energy level, number of shocks/pulses, and frequency of the shocks/pulses) may be applicable to a specific hard or soft tissue, or to different respective portions of a particular tissue, to achieve desirable cleaning Referring to FIG. 15, in the case of a tissue that has a larger volume, the cleaning process in certain embodiments includes the movement of the applicator 20 and reflector 22 with its associated focal volume 25 along the tissue surface to allow the cleaning of the whole tissue sample 140.

The movement can be done manually or automatically by a controller actuated by a software program, on an applicator movement path/pattern 155 between the applicator starting position 150 and applicator ending position 159.

If the thickness of the tissue sample is higher than the length of the focal volume, the harvested tissue can be treated on both sides with the same movement of the applicator 20 and reflector 22 with its associated focal volume 25 along both tissue surfaces to allow the cleaning of the whole tissue sample 140. The movements can be done manually or automatically by a controller actuated by a software program.

Cleaning/Tenderizing of Animal Meat

Pressure shock waves can also be used in embodiments of the invention to clean germs or micro-organisms from animal meat. Using a set-up as generally described in FIGS. 14 and 15, the meat can be concomitantly or sequentially cleaned and/or tenderized in a short period of time, which is very important for prime cuts. Using the pressure shock wave for tenderizing it can be avoided to keep the meat refrigerated for prolonged time intervals (days to weeks) in specialized rooms for tenderizing, which can reduce the expenses (energy and capital costs) associated with such prime cuts. Scientific literature has reported successful results in tenderizing the meats using specific blasting pressure shock waves. This technique has significant drawbacks (use of dangerous explosive devices, large and very strong containers to contain explosions, etc.) that can be eliminated by using electrohydraulic generated pressure shock waves.

Figure 16A:
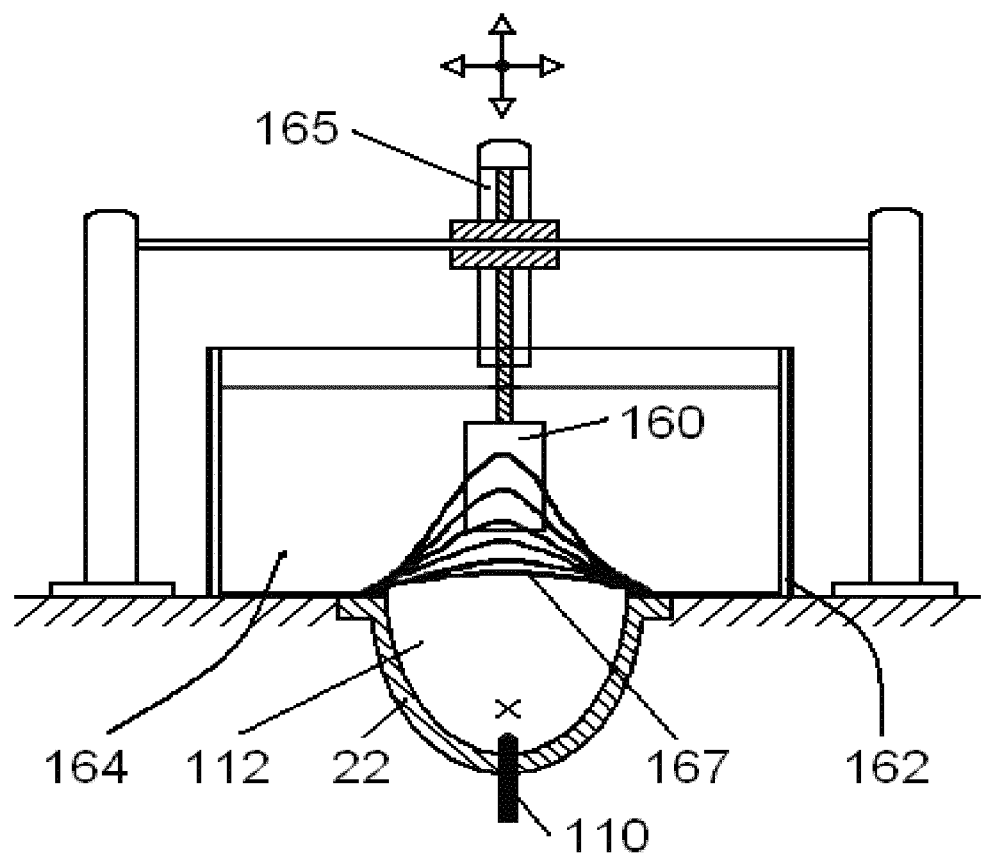
FIG. 16A is a cross-sectional schematic diagram of an electrohydraulic shock wave device with a meat moving mechanism in one embodiment of the present invention.
Figure 16B:
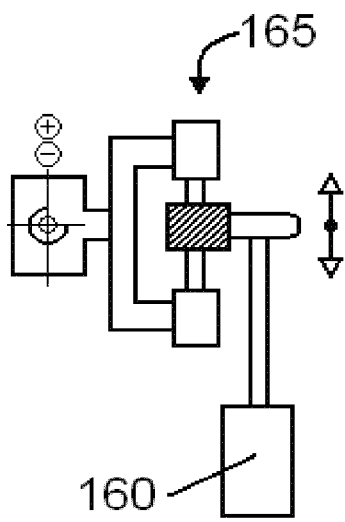
FIG. 16B is a schematic diagram of a meat moving mechanism in one embodiment of the present invention.

The usage of pressure shock waves for cleaning animal meat from germs or micro-organisms and/or tenderizing using an electrohydraulic device is presented in one embodiment in FIGS. 16A and 16B. Set-ups similar to the electrohydraulic devices can be created using electromagnetic or piezoelectric (using piezoelectric crystals or fibers) technologies.

The pressure shock waves generated using these principles (electrohydraulic, electromagnetic or piezoelectric) generate lower pressure gradients when compared to the blast pressure shock waves described in prior art uses. To put the same amount of energy in the target as the blast pressure shock waves, in the case of using electrohydraulic, electromagnetic or piezoelectric generators a larger number of shocks are applied (between 24 to 500 pulses per cm$^3$ of meat) and with energies delivered in the targeted area of 0.20 to 0.80 mJ/mm$^2$. By comparison, the blast pressure shock waves are radial in nature (unfocused) which means that the highest pressure is found near the source and the energy fades away when the pressure shock waves increase their distance from the source, which gives an exponential decay of the pressures inside the targeted volume. Focused shock wave devices can control the treatment region and can generate very high pressures in the focal volume 25 and thus provide high energies into the target.

For both cleaning and/or tenderizing processes, meat 160 can be sealed in vacuum bags and then placed inside the treatment tank 162 filled with fluid/water 164, as shown in FIG. 16A. The pressure shock waves 167 are generated by the high voltage discharge in between the opposing electrodes 110, found at the bottom of the reflector 22 that is used to reflect and focus the pressure shock waves 167 towards the vacuum bag with meat 160 placed inside the treatment tank 162. The transmission of the shock waves without attenuation is done via the water/propagation medium 112 and tank fluid/water 164 in which the vacuum bag with meat 160 was placed.

To move the vacuum bag with meat 160 in the focal zone of the shock wave device, a two-dimensional moving mechanism 165 can be employed, as shown in FIGS. 16A and 16B. The moving mechanism 165 can use screw/nut systems or a gears, etc. and can be completely automated and computerized (controlled by computers).

For cleaning process embodiments meat is treated at high energy settings (energy flux densities between 0.20 and 0.80 mJ/mm$^2$) and using 100 to 500 pulses per cm$^3$ of meat.

For tenderizing process embodiments meat is treated at high energy settings (energy flux densities between 0.40 and 0.80 mJ/mm$^2$) and using 24 to 500 pulses per cm$^3$ of meat.

Cleaning of Industrial, Dirty and Polluted Waters

Figure 17:
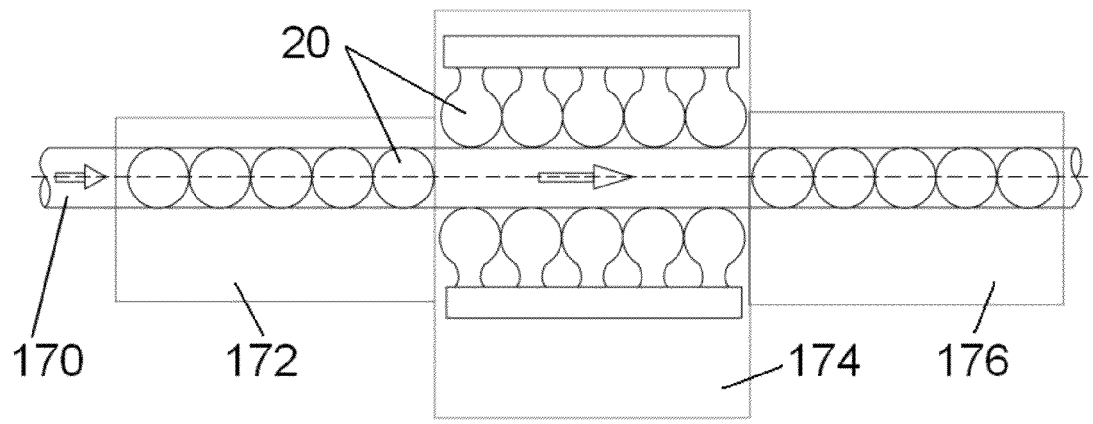
FIG. 17 is a schematic diagram of multiple shock wave applicators positioned along an industrial fluid filtration pipe in one embodiment of the present invention.

Referring to FIG. 17, pressure shock waves are used in embodiments of the invention for cleaning industrial, dirty or polluted waters. Large, powerful, shock wave applicators 20 are mounted along the cleaning fluid filtration pipe 170. The applicators 20 are grouped in clusters formed of ten (10) applicators 20 with two opposing groups of five (5) consecutive applicators 20.

Multiple clusters of applicators 20 are mounted along the fluid filtration pipe 170 in which the fluid that needs cleaning moves at a slow speed, as indicated by the arrow. A first reflectors' cluster 172, a second reflectors' cluster 174 and a third reflectors' cluster 176 provide consecutive clusters which are positioned with a rotation of 90 degrees relative to the previous cluster. Such embodiment provides ease for access and maintenance.

The number of shocks required for industrial cleaning embodiments is 10,000 to 100,000 or more at settings of 20-30kV (discharge voltage in $F_1$). In embodiments, energy flux densities of higher than 0.4 mJ/mm² and at frequencies (number of pulses per second) equal or higher than 1 Hz are provided.

Piezoelectric or electromagnetic systems are well-suited for industrial cleaning application to avoid the changing of the electrodes 110 when they reach their end of life. The gap between tips in electrohydraulic devices when wearing to the end of life is large enough to prevent the normal high voltage discharge between tips and thus preventing the formation of shock waves. Typical electrohydraulic applicators 20 can be used between 20,000 and up to 100,000 possible discharges, before they require the change of the electrodes 110.

Figure 18:
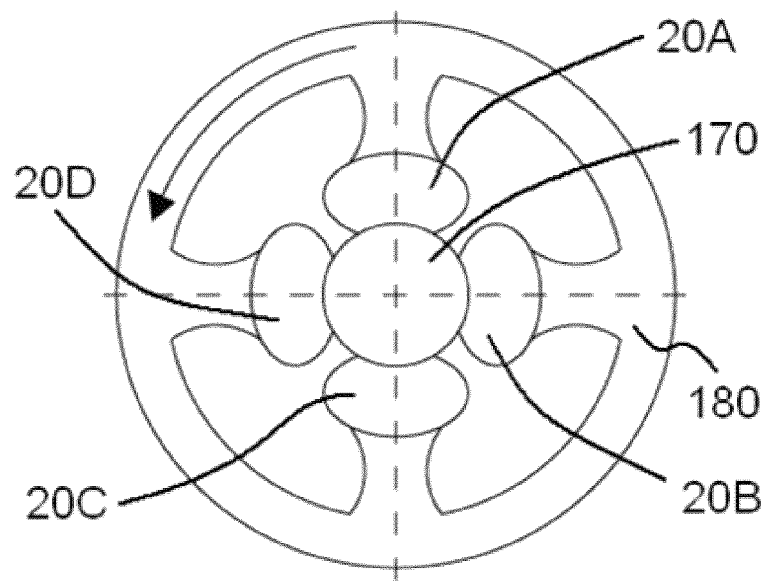
FIG. 18 is a top cross-sectional top schematic diagram of a rotatable shock wave applicators' wheel positioned around a filtration pipe in one embodiment of the present invention.

FIG. 18 shows an embodiment of the invention including toroidal filtration with applicators 20A, 20B, 20C and 20D mounted on the applicators' wheel 180, which has a rotational movement as indicated by the arrow. The applicators' wheel 180 moves at a calculated low speed, to allow the uniformly deposit of energies into the fluid filtration pipe 170 in order to achieve the proper cleaning of the industrial, dirty or polluted waters. Multiple toroidal units can be mounted along the fluid filtration pipe 170 for improved efficiency and for allowing targeted cleaning against different types of contaminants, by fine tuning each toroidal unit 170 for a special contaminant that needs to be eliminated during cleaning of the industrial, dirty or polluted waters.

Figure 19:
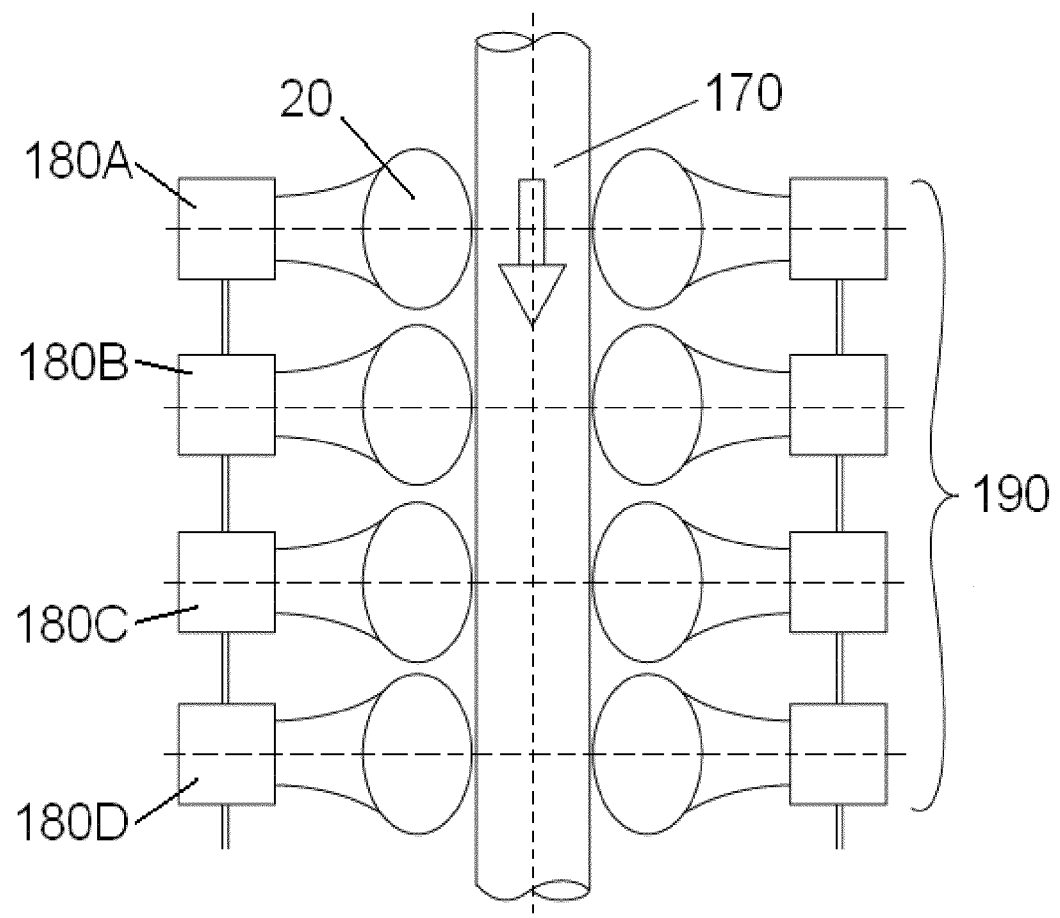
FIG. 19 is a cross-sectional schematic diagram of a vertical battery of shock wave applicators' wheels' along a filtration pipe in one embodiment of the present invention.

FIG. 19 shows an embodiment of the invention including vertical battery of applicators' clusters 190 composed of toroidal filtration units (FIG. 18). To achieve this construction, multiple applicators' wheels 180A, 180B, 180C and 180D are grouped and driven around the fluid filtration pipe 170 through which the fluid that needs filtration moves at low speeds to allow the complete filtration process provided by the applicators 20 present on the multiple applicators' wheels 180A, 180B, 180C and 180D. The applicators 20 are constructed with reflectors 22 (not shown in FIGS. 17, 18 and 19) that can be an ellipsoid, paraboloid, spheroid, or have any other full rotational shape, which can be used to focus the shock waves in the treatment/cleaning area.

Figure 20:
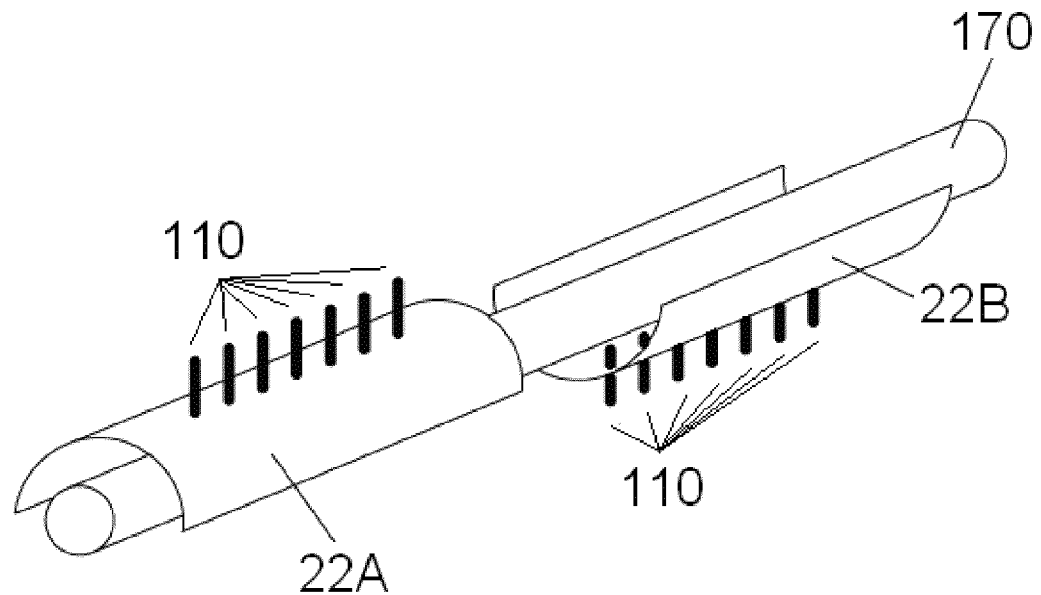
FIG. 20 is a schematic diagram of tubular shock wave reflectors including multiple electrodes positioned along a filtration pipe in one embodiment of the present invention.

FIG. 20 shows an embodiment with semi-tubular reflectors 22A and 22B (part of a tube with a parabolic, ellipsoidal or round cross-section), which are used to focus the shock waves generated by the high voltage discharge across opposing electrodes 110. This construction can create pressure gradients inside the fluid filtration pipe 170 through which the industrial, sewer or polluted waters are circulated in the cleaning station. For this embodiment, an increased number of shocks and/or high energy settings may be used to compensate for the lost in reflective area for reflectors 22A and 22B when compared with normal semi-ellipsoidal reflectors 22. This supposition is based on the fact that the energy delivered in the focal volume 25 (not shown in FIG. 20) is direct proportional to the reflective area used to focus the pressure shock waves in the treatment/cleaning area. The same construction as the one presented in FIG. 20 can use devices that generate pressure shock waves using the piezoelectric or electromagnetic principle.

Figure 21:
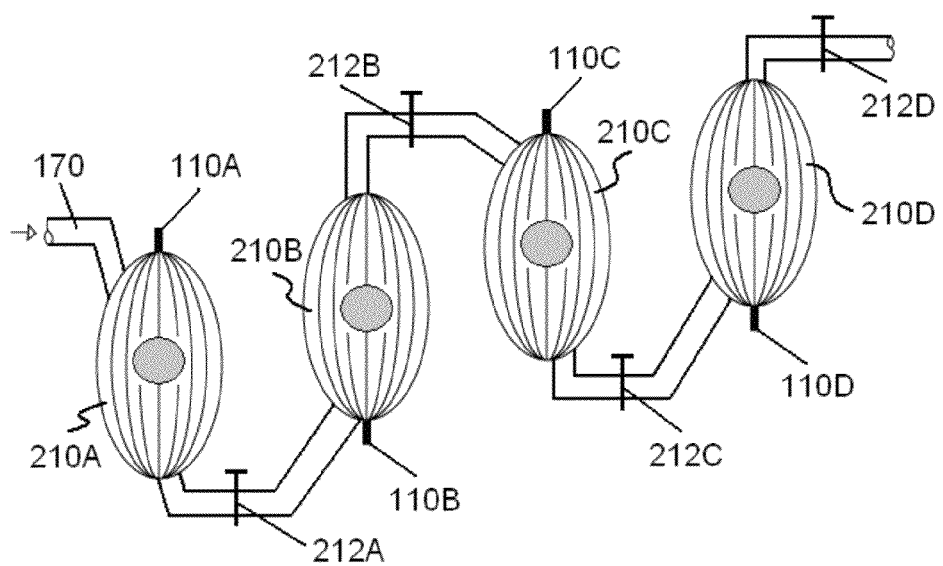
FIG. 21 is schematic diagram of a series of shock wave applicators in a valve-controlled piped fluid treatment system in one embodiment of the present invention.

Referring to FIG. 21, pressure shock waves applicators 210A, 210B, 210C and 210D, such as with ellipsoid geometry, are mounted in series to maximize the filtration effect. These larger ellipsoids in some embodiments can take 10L and up to 100L or more of fluid and allow 100% of reflection area for pressure shock waves generated using electrodes 110A, 110B, 110C and 110D. The killing of the micro-organisms, bacteria, and the like, can be done by the pressure gradients created inside the applicators 210A, 210B, 210C and 210D. Also, based on the targeted micro-organisms to be killed, the applicator 210A can have a different geometry from the applicators 210B, 210C and 210D. In fact, different geometries can be found in each applicator 210A, 210B, 210C and 210D, which creates a system for filtration that targets all type of micro-organisms and bacteria found in sewer, dirty, industrial and polluted waters. In other words, in the applicator 210A, a particular type of micro-organism is killed, in the applicator 210B another type, in the applicator 210C another type and so on. To allow sufficient time for treatment in each applicator (210A, 210B, 210C and 210D), a system of filtration pipe valves 212A, 212, 212C and 211D is used to be able to isolate each applicator 210A, 210B, 210C and 210D. By putting these different types of applicators 210A, 210B, 210C and 210D in series, with each of them designed to target and kill different microorganisms, allows the sewer, dirty, industrial and polluted waters to reach a high level of cleanliness when exiting the treatment plant. This array of ellipsoids can also be combined with other types of filtrations systems using charcoal, ozone, ultraviolet light, and the like.

The use of multiple clusters with possible redundant action (FIGS. 17, 19, 20 and 21) allows the change of electrodes 110 without interruption of the filtration process when an electrohydraulic approach is used or allows the change of an entire cluster if a failure of the applicators 20 may occur when the electrohydraulic, electromagnetic or piezoelectric approach is used.

Cleaning and Preservation of Food Liquids

Embodiments of the invention used for blood cleaning/sterilization can be adapted to clean bacteria or other organisms from a variety of other fluids, such as liquid foods including milk, natural juices, wines, and the like. This use of pressure shock waves may better preserve the taste of these fluids, due to the absence of heat or chemicals used in existing processes employed for cleaning and preservation of food liquids.

The use of shock waves for commercial cleaning and preservation of food liquids, in order to be economical needs to sterilize large quantities of fluids, which mean that the cleaning/sterilization process must be applied to the fluids when they flow through a pipe/tube in front of the shock wave applicators 20. Accordingly, embodiments presented in FIGS. 1, 3A, 3B, 6A, 6B, 7, 8 and 10 can be applied to accomplish the cleaning and preservation of food liquids such as milk, juices, etc.

For this application, special large reflectors 22 can also be implemented such as the reflector used for industrial applications (see FIGS. 17, 18, 19, 20 and 21).

The settings used for commercial cleaning and preservation of food liquids can use energy flux densities between 0.10 to 0.80 mJ/mm² and using 100 to 1,500 pulses per cm³ of food liquids.

While the invention has been described with reference to exemplary structures and methods in some embodiments of the invention, the invention is not intended to be limited thereto, but to extend to modifications and improvements within the scope or equivalence of such claims to the invention.

What is claimed is:

1. A method comprising;
   providing a volume of fluid in a treatment tank, wherein the treatment tank includes a shock wave applicator configured to have a focal volume disposed in the volume of fluid;
   sealing an animal meat including biological contaminants in a vacuum bag;

submerging the animal meat in the bag into the volume of fluid, wherein at least a portion of the animal meat is in the focal volume of the shock wave applicator; and applying a plurality of pressure shock wave pulses, by the shock wave applicator, to the animal meat in the volume of fluid in sufficient amounts to perform at least one of damaging at least some of the biological contaminants in the animal meat and tenderizing the animal meat.

2. The method of claim 1, further comprising moving the animal meat through the focal volume of the shock wave applicator during applying the plurality of pressure shock wave pulses.

3. The method of claim 2, wherein the moving of the shock wave generator is performed manually.

4. The method of claim 2, wherein the moving of the shock wave applicator is controlled by a controller actuated by a computer.

5. The method of claim 2, wherein the shock wave applicator applies between 100 and 500 pressure shock wave pulses per $cm^3$ of animal meat at an energy flux density between 0.20 and 0.80 $mJ/mm^2$ to damage at least some of the biological contaminants in the animal meat.

6. The method of claim 2, wherein the shock wave applicator applies between 24 and 500 pressure shock wave pulses per $cm^3$ of animal meat at an energy flux density between 0.40 and 0.80 $mJ/mm^2$ to tenderize the animal meat.

7. The method of claim 2, wherein the shock wave applicator applies between 100 and 500 pressure shock wave pulses per $cm^3$ of animal meat at an energy flux density between 0.40 and 0.80 $mJ/mm^2$ to damage at least some of the biological contaminants in the animal meat and tenderize the animal meat.

8. The method of claim 2, wherein the shock wave applicator includes one of an electrohydraulic shock wave generator, an electromagnetic shock wave generator, a shock wave generator including piezoelectric crystals, and shock wave generator including piezoelectric fibers.

9. The method of claim 2, wherein the fluid is water.

10. The method of claim 2, wherein the biological contaminants include at least one of bacteria, viruses, and microorganisms.

11. The method of claim 1, wherein the shock wave applicator applies between 100 and 500 pressure shock wave pulses per $cm^3$ of animal meat at an energy flux density between 0.20 and 0.80 $mJ/mm^2$ to damage at least some of the biological contaminants in the animal meat.

12. The method of claim 1, wherein the shock wave applicator applies between 24 and 500 pressure shock wave pulses per $cm^3$ of animal meat at an energy flux density between 0.40 and 0.80 $mJ/mm^2$ to tenderize the animal meat.

13. The method of claim 1, wherein the shock wave applicator applies between 100 and 500 pressure shock wave pulses per $cm^3$ of animal meat at an energy flux density between 0.40 and 0.80 $mJ/mm^2$ to damage at least some of the biological contaminants in the animal meat and tenderize the animal meat.

14. The method of claim 1, wherein the shock wave applicator includes one of an electrohydraulic shock wave generator, an electromagnetic shock wave generator, a shock wave generator including piezoelectric crystals, and shock wave generator including piezoelectric fibers.

15. The method of claim 1, wherein the of fluid is water.

16. The method of claim 1, wherein the biological contaminants include at least one of bacteria, viruses, and microorganisms.

17. A method of comprising:

providing a volume of fluid in a treatment tank, wherein the treatment tank includes a shock wave applicator configured to have a focal volume disposed in the volume of fluid;

submerging an animal meat including biological contaminants into the volume of fluid in direct contact with the fluid in the treatment tank, wherein at least a portion of the animal meat is in the focal volume of the shock wave applicator; and applying a plurality of pressure shock wave pulses, by the shock wave applicator, to the animal meat in the volume of fluid in sufficient amounts to perform at least one of damaging at least some of the biological contaminants in the animal meat and tenderizing the animal meat.

18. The method of claim 17, further comprising moving the animal meat through the focal volume of the shock wave applicator during applying the plurality of pressure shock wave pulses.

19. The method of claim 17, wherein the shock wave applicator applies between 24 and 500 pressure shock wave pulses per $cm^3$ of animal meat at an energy flux density between 0.40 and 0.80 $mJ/mm^2$ to tenderize the animal meat.

20. The method of claim 19, wherein the fluid is water.

* * * * *